(12) United States Patent
Crofts et al.

(10) Patent No.: US 11,813,082 B2
(45) Date of Patent: Nov. 14, 2023

(54) METHOD OF CONTROLLING ACCESS TO ACTIVITY DATA FROM A GARMENT

(71) Applicant: Prevayl Innovations Limited, Manchester (GB)

(72) Inventors: Adam Lee Edward Crofts, Manchester (GB); Tahir Mahmood, Manchester (GB)

(73) Assignee: Prevayl Innovations Limited, Manchester (GB)

( * ) Notice: Subject to any disclaimer, the term of this patent is extended or adjusted under 35 U.S.C. 154(b) by 0 days.

(21) Appl. No.: 17/432,583

(22) PCT Filed: Jun. 5, 2020

(86) PCT No.: PCT/GB2020/051360
§ 371 (c)(1),
(2) Date: Aug. 20, 2021

(87) PCT Pub. No.: WO2020/245595
PCT Pub. Date: Dec. 10, 2020

(65) Prior Publication Data
US 2022/0142572 A1    May 12, 2022

(30) Foreign Application Priority Data
Jun. 7, 2019   (GB) .................................... 1908181

(51) Int. Cl.
*G16H 10/60*    (2018.01)
*A61B 5/00*    (2006.01)
(Continued)

(52) U.S. Cl.
CPC ............ *A61B 5/6804* (2013.01); *A41D 1/002* (2013.01); *A41D 13/1281* (2013.01);
(Continued)

(58) Field of Classification Search
CPC ....................................................... G16H 10/60
See application file for complete search history.

(56) References Cited

U.S. PATENT DOCUMENTS 9,554,721 B1    1/2017  Zikov et al.
10,499,849 B1   12/2019 Chuang
(Continued)

FOREIGN PATENT DOCUMENTS

CN    204351118 U    5/2015
CN    206166913 U    5/2017
(Continued)

OTHER PUBLICATIONS

GB Search Report dated Dec. 9, 2019 of GB Application 1908181.9.
(Continued)

*Primary Examiner* — John A Pauls
(74) *Attorney, Agent, or Firm* — HALEY GUILIANO LLP

(57) ABSTRACT

An image of a garment is obtained (101). The garment comprises a marker located on an outside surface of the garment. The marker comprises a code string identifying the garment encoded into a visual symbol. The image is processed to generate a data string representing the visual symbol (102). The data string is used to access activity data associated with a sensor of the garment identified by the code string. The system comprises the garment and one or more electronic devices operable to perform the method.

17 Claims, 8 Drawing Sheets

(51) Int. Cl.
  *G16H 20/30* (2018.01)
  *G16H 40/67* (2018.01)
  *G16H 15/00* (2018.01)
  *G06F 16/955* (2019.01)
  *G06V 40/10* (2022.01)
  *G06V 20/00* (2022.01)
  *A41D 1/00* (2018.01)
  *A41D 13/12* (2006.01)
  *A61B 5/11* (2006.01)
  *G06F 21/32* (2013.01)
  *G06F 21/62* (2013.01)
  *H04L 9/40* (2022.01)
  *G06F 21/31* (2013.01)

(52) U.S. Cl.
  CPC .......... *A61B 5/0022* (2013.01); *A61B 5/1114* (2013.01); *A61B 5/1118* (2013.01); *G06F 16/9554* (2019.01); *G06F 21/31* (2013.01); *G06F 21/32* (2013.01); *G06F 21/6227* (2013.01); *G06F 21/6245* (2013.01); *G06V 20/95* (2022.01); *G06V 40/10* (2022.01); *G16H 10/60* (2018.01); *G16H 15/00* (2018.01); *G16H 20/30* (2018.01); *G16H 40/67* (2018.01); *H04L 63/0428* (2013.01)

(56) References Cited

U.S. PATENT DOCUMENTS

| | | | |
|---|---|---|---|
| 11,557,397 B2 | 1/2023 | Crofts et al. | |
| 2004/0171956 A1 | 9/2004 | Babashan | |
| 2007/0208233 A1 | 9/2007 | Kovacs | |
| 2008/0125288 A1 | 5/2008 | Case | |
| 2008/0218310 A1* | 9/2008 | Alten | A43B 5/00 702/182 |
| 2009/0030333 A1 | 1/2009 | McDonough | |
| 2009/0069702 A1 | 3/2009 | How et al. | |
| 2009/0112072 A1* | 4/2009 | Banet | A61B 5/0205 600/301 |
| 2009/0192823 A1* | 7/2009 | Hawkins | G06Q 10/06 715/767 |
| 2010/0280331 A1 | 11/2010 | Kaufman et al. | |
| 2010/0292050 A1 | 11/2010 | Dibenedetto et al. | |
| 2010/0292599 A1 | 11/2010 | Oleson et al. | |
| 2011/0062237 A1 | 3/2011 | Chaves | |
| 2012/0146784 A1* | 6/2012 | Hines | A42B 3/046 2/2.5 |
| 2012/0235821 A1 | 9/2012 | Dibenedetto et al. | |
| 2012/0246795 A1 | 10/2012 | Scheffler et al. | |
| 2012/0306643 A1 | 12/2012 | Dugan | |
| 2013/0120106 A1 | 5/2013 | Cauwels et al. | |
| 2013/0175334 A1* | 7/2013 | Miller | G16H 10/60 235/375 |
| 2014/0040626 A1* | 2/2014 | Fredinburg | G06F 21/6254 713/182 |
| 2014/0125619 A1 | 5/2014 | Panther et al. | |
| 2014/0135644 A1 | 5/2014 | Kim | |
| 2014/0221855 A1 | 8/2014 | McCaffrey | |
| 2014/0275876 A1* | 9/2014 | Hansen | G16Z 99/00 600/323 |
| 2014/0288436 A1 | 9/2014 | Venkatraman et al. | |
| 2014/0318699 A1 | 10/2014 | Longinotti-Buitoni et al. | |
| 2014/0323827 A1 | 10/2014 | Ahmed et al. | |
| 2015/0061889 A1 | 3/2015 | Kotaki et al. | |
| 2015/0061891 A1 | 3/2015 | Oleson et al. | |
| 2015/0081169 A1 | 3/2015 | Pisz | |
| 2015/0088002 A1 | 3/2015 | Podhajsky et al. | |
| 2015/0099991 A1 | 4/2015 | Yamaguchi et al. | |
| 2015/0182841 A1 | 7/2015 | Martikka et al. | |
| 2015/0230752 A1* | 8/2015 | Fort | A41D 13/1281 600/301 |
| 2015/0231481 A1 | 8/2015 | Jones et al. | |
| 2015/0305674 A1 | 10/2015 | McPherson et al. | |
| 2016/0058313 A1 | 3/2016 | Sato | |
| 2016/0098581 A1* | 4/2016 | Martí Ascencio | G06Q 10/00 340/5.82 |
| 2016/0120460 A1 | 5/2016 | Eom | |
| 2016/0134642 A1* | 5/2016 | Hamid | H04L 63/045 713/160 |
| 2016/0135516 A1 | 5/2016 | Cobbett et al. | |
| 2016/0159106 A1 | 6/2016 | De Castro | |
| 2016/0192716 A1 | 7/2016 | Lee | |
| 2016/0256104 A1 | 9/2016 | Romem et al. | |
| 2016/0371438 A1* | 12/2016 | Annulis | G06F 21/32 |
| 2016/0374588 A1 | 12/2016 | Shariff et al. | |
| 2017/0031435 A1 | 2/2017 | Raffle et al. | |
| 2017/0071548 A1 | 3/2017 | Wiebe et al. | |
| 2017/0086519 A1 | 3/2017 | Vigano' et al. | |
| 2017/0094216 A1* | 3/2017 | Ekambaram | A61B 5/0077 |
| 2017/0140120 A1* | 5/2017 | Thrower | G16H 40/67 |
| 2017/0181703 A1 | 6/2017 | Kaib et al. | |
| 2017/0196513 A1 | 7/2017 | Longinotti-Buitoni et al. | |
| 2017/0243615 A1 | 8/2017 | Tabak | |
| 2017/0303864 A1 | 10/2017 | Su | |
| 2017/0332946 A1 | 11/2017 | Kikkeri | |
| 2017/0368413 A1 | 12/2017 | Shavit | |
| 2018/0092698 A1* | 4/2018 | Chopra | A61B 90/39 |
| 2018/0174683 A1 | 6/2018 | Franz et al. | |
| 2018/0228406 A1 | 8/2018 | Mendelsohn | |
| 2018/0232925 A1* | 8/2018 | Frakes | A61B 90/36 |
| 2018/0300919 A1* | 10/2018 | Muhsin | G16H 50/50 |
| 2018/0345079 A1 | 12/2018 | Lindman et al. | |
| 2018/0353152 A1 | 12/2018 | Teji | |
| 2018/0358119 A1 | 12/2018 | Bhushan et al. | |
| 2019/0000384 A1 | 1/2019 | Gupta et al. | |
| 2019/0037932 A1 | 2/2019 | Martin et al. | |
| 2019/0053469 A1 | 2/2019 | Mardirossian | |
| 2019/0090765 A1 | 3/2019 | Cuccinello | |
| 2019/0196411 A1 | 6/2019 | Yuen | |
| 2019/0246734 A1 | 8/2019 | Nurse et al. | |
| 2020/0333837 A1 | 10/2020 | Weiner | |
| 2020/0367758 A1 | 11/2020 | Kimura et al. | |
| 2022/0101994 A1 | 3/2022 | Crofts et al. | |
| 2023/0115286 A1 | 4/2023 | Crofts et al. | |

FOREIGN PATENT DOCUMENTS

| | | | |
|---|---|---|---|
| CN | 208624750 U | 3/2019 | |
| CN | 110584627 A | 12/2019 | |
| CN | 209928492 U | 1/2020 | |
| CN | 111035376 A | 4/2020 | |
| EP | 3332698 A1 | 6/2018 | |
| EP | 3431146 A1 | 1/2019 | |
| GB | 2476690 A | 7/2011 | |
| GB | 2561575 A | 10/2018 | |
| GB | 2563065 A | 12/2018 | |
| GB | 2565330 A | 2/2019 | |
| GB | 2567533 A | 4/2019 | |
| GB | 2586950 A | 3/2021 | |
| GB | 2590985 A | 7/2021 | |
| GB | 2590986 A | 7/2021 | |
| GB | 2591819 A | 8/2021 | |
| GB | 2593433 A | 9/2021 | |
| GB | 2593434 A | 9/2021 | |
| GB | 2596157 A | 12/2021 | |
| GB | 2596158 A | 12/2021 | |
| GB | 2596782 A | 1/2022 | |
| GB | 2596783 A | 1/2022 | |
| JP | 2015-073807 A | 4/2015 | |
| KR | 101907383 | 10/2018 | |
| WO | 00/04522 A1 | 1/2000 | |
| WO | 2006/009830 A2 | 1/2006 | |
| WO | 2008/038141 A2 | 4/2008 | |
| WO | 2012/167026 A2 | 12/2012 | |
| WO | 2014/192002 A1 | 12/2014 | |
| WO | 2015/056262 A1 | 4/2015 | |
| WO | 2017/198978 A1 | 11/2017 | |
| WO | WO 2018134432 | 7/2018 | |
| WO | WO-2018134432 A1 * | 7/2018 | A61B 5/6801 |
| WO | 2018/145719 A1 | 8/2018 | |
| WO | 2018/152475 A1 | 8/2018 | |

(56) References Cited

FOREIGN PATENT DOCUMENTS

| WO | 2019/086908 A1 | 5/2019 |
|---|---|---|
| WO | 2019/104374 A1 | 6/2019 |
| WO | 2019/223919 A1 | 11/2019 |

OTHER PUBLICATIONS

GB 1st Examination Report dated Mar. 16, 2020 of GB Application 1908181.9.
GB 2nd Examination Report dated Apr. 16, 2021 of GB Application 1908181.9.
International Search Report and Written Opinion of PCT/GB2020/051360 dated Aug. 20, 2020.
"Enflux exercise clothing", kickstarter.com, [online] available from https://www.kickstarter.com/projects/1850884998/enflux-smart-clothing-3d-workout-tracking-and-form/description.
"EMGlare Heart" emglare.com, [online] available from https://emglare.com/.
YouTube Video, titled "QR Code & Bluetooth Connection Tutorial with Shimmer", purportedly uploaded by "Shimmer Sensing" on Feb. 6, 2014, available from https://www.youtube.com/watch?v=16pZLr2h9ag Screenshot provided (taken on Aug. 13, 2021).
Examination Report received in GB1908187.6 dated May 29, 2020.
GB Combined Search Report and Examination Report dated Dec. 12, 2019 of GB Application 1908187.6.
GB Combined Search Report and Examination Report of GB Application 2001804.0 dated Aug. 21, 2020.
International Search Report and Written Opinion of PCT/GB2020/051361 dated Aug. 4, 2020.
International Search Report and Written Opinion received for PCT Patent Application No. PCT/GB2021/050284, dated Apr. 12, 2021, 13 pages.
International Search Report and Written Opinion received for PCT Patent Application No. PCT/GB2021/050285, dated Apr. 30, 2021, 13 pages.
International Search Report and Written Opinion received for PCT Patent Application No. PCT/GB2021/051489, dated Sep. 20, 2021, 11 pages.
Lightbody et al., A versatile high-performance visual fiducial marker detection system with scalable identity encoding, Apr. 3, 2017, pp. 276-282, Publisher: Proceedings of the Symposium on Applied Computing.
Naked Labs (https://nakedlabs.com/naked-home-body-scanner, available at least from Oct. 4, 2018, 2 pages) (Year: 2018).
Peter Lightbody et al: "A versatile high-performance visual fiducial marker detection system with scalable identity encoding", Applied Computing, ACM, 2 Penn Plaza, Suite 701 New York NY 10121-0701 USA, Apr. 3, 2017 pp. 276-282, XP058337320.

\* cited by examiner

METHOD OF CONTROLLING ACCESS TO ACTIVITY DATA FROM A GARMENT

CROSS-REFERENCE TO RELATED APPLICATIONS

This application is a national stage application under 35 U.S.C. § 371 of International Application PCT/GB2020/051360, filed Jun. 5, 2020, which claims priority of GB Patent Application 1908181.9 filed Jun. 7, 2019. The disclosure of which are hereby incorporated by reference herein in their entireties.

BACKGROUND

The present invention is directed towards a method, garment and system. The present invention is directed in particular towards accessing activity data associated with a sensor incorporated into the garment.

Garments incorporating sensors are wearable electronics designed to interface with a wearer of the garment, and to determine information such as the wearer's heart rate, rate of respiration, activity level, and body positioning. Such properties can be measured with a sensor assembly that includes a sensor for signal transduction and/or microprocessors for analysis. Such garments are commonly referred to as 'smart clothing'. It would be desirable to provide a mechanism for controlling access to the data obtained from the sensors located on the garment.

SUMMARY

According to the present disclosure there is provided a method, garment and system as set forth in the appended claims. Other features of the invention will be apparent from the dependent claims, and the description which follows.

According to a first aspect of the invention, there is provided a method. The method comprises obtaining an image of a garment. The garment comprises a marker located on an outside surface of the garment. The marker comprises a code string identifying the garment encoded into a visual symbol. The method comprises processing the image to generate a data string representing the visual symbol. The method comprises using the data string to access activity data associated with a sensor of the garment identified by the code string.

Significantly, a garment comprising a marker is provided. The marker comprises a (unique) code string identifying the garment encoded into a visual symbol. When the visual symbol is imaged and the data string is obtained from the image, the data string is used to access activity data associated with the garment. In this way, access to the activity data for the garment may be controlled by imaging the garment and processing the resultant image. The method therefore enables the access of activity data to be controlled using a simple electronic device such as a portable electronic device with an integrated camera. As a result, an electronic device which may not be in direct communication with the garment is able to access activity data in a controlled way by imaging the garment and processing the resultant image. Beneficially, access to the data obtained from the sensor(s) located on the wearer's garment is controlled through a simple and intuitive procedure of imaging the garment. This approach enables different electronic devices to access activity data associated with the garment in a controlled way.

Providing the marker on the outside surface of the garment means that the activity data can be accessed from an external device at a distance while the garment is being worn. For example, a personal trainer may use their mobile phone to capture images of the wearer of the garment while the wearer is undertaking exercise. Because the marker is located on an outside surface of the garment, a data string representation of the marker can be extracted from the captured images and used to obtain activity data sensed by sensors of the garment.

Advantageously still, the method according to the present invention enables a user such as a personal trainer to monitor several different people wearing garments according to the present invention at the same time. The simple act of the personal trainer moving the mobile phone camera from a first user to a second user allows the personal trainer to switch from obtaining (and potentially viewing) activity data associated with the first user to obtaining (and potentially viewing) activity data associated with the second user. The present invention therefore provides an easy and intuitive mechanism for enabling an external device to obtain access to activity data from a garment.

Advantageously still, the marker located on the outside surface of the garment can be used as a marker for motion tracking. This allows for the display of augmented reality objects representing activity data obtained from the sensors over a live view image shown on the external device.

Using the data string to access activity data associated with a sensor of the garment identified by the code string may involve establishing direct communication between the garment and the electronic device performing the method. This may involve pairing the garment to the electronic device performing the method using the code string identifying the garment. This may involve using the code string identifying the garment to listen out for activity data broadcast by the garment. The pairing may be performed over a known short-range communication protocol such as near-field communication, Bluetooth®, Bluetooth® Low Energy, Bluetooth® Mesh, or Bluetooth® 5, or ZigBee®. The code string may comprise a communication address for the garment or a component of a communication address for the garment. The code string may identify an electronics component of the garment such as a (removable) electronics module of the garment.

Using the data string to access the activity data may comprise establishing, based on the data string, the identity of the garment, and may further comprise accessing the activity data associated with the sensor of the identified garment. The establishing step may be performed by a user electronic device or the server.

Establishing, based on the data string, the identity of the garment may comprises decoding the data string so as to obtain the code string and may further comprises identifying the garment based on the code string. The data string may be a simple digitised representation of the visual symbol or may be an encrypted version of the code string. The method may run a decoding algorithm to generate the code string from the data string. The decoding and identifying steps may be performed by the user electronic device or the server.

A database may be provided which may store one or a plurality of code strings each associated with a different garment. The identity of the garment may be established based on which of the code strings in the database the generated data string (once decoded) matches. The database may be maintained on the electronic device performing the method or may be a remote database that the electronic device has access to.

The method may further comprise obtaining a user credential from a user. The activity data may only be accessed if the user is authorised, based on the obtained user credential, as having permission to access the activity data. In this way, access to the activity data is controlled such that only a user with the requisite user credential is able to access the activity data. The activity data may only be accessed if the user is authorised as having permission to access the activity data. The user credential may be in the form of a password or passcode. The user credential may be in the form of biometric data. The biometric data may be obtained by obtaining one or more of a fingerprint, palm print, iris scan, or facial image of the user. Other forms of biometric data are within the scope of the present disclosure.

The method may further comprise determining, based on the obtained user credential, whether the user is authorised to access the activity data. The method may further comprise providing the activity data to the user only if the user is authorised. The steps of determining and providing may be performed by a user electronic device or a server. Different users may have different permissions levels and thus may have permission to access different quantities or types of activity data. For example, a coach or personal trainer may have access to a first set of data from the garment whereas a medical professional may have access to a greater range and type of data from the garment. The method may comprise determining, from the user credential, the permission level of the user, and may comprise providing the activity data to the user based on the determined permission level The method may be performed by a user electronic device. The method may be performed by a user electronic device cooperating with a server.

Using the data string to access activity data associated with a sensor of the garment identified by the code string may comprise the user electronic device transmitting the data string to a server so that the server is able to establish the identity of the garment from the data string. The user electronic device may receive, from the server, the activity data.

The method may further comprise the user electronic device obtaining a user credential from a user. The activity data may only be accessed if the user is authorised, based on the obtained user credential, as having permission to access the activity data.

The method may further comprise the user electronic device transmitting the user credential to a server so that the server is able to determine if the user is authorised as having permission to access the activity data based on the obtained user credential. Using the data string to access the activity data may further comprise the user electronic device receiving, from the server, the activity data if the user is authorised the server as having permission to access the activity data.

The marker may be a fiducial marker. Beneficially, a fiducial marker is useable as a point of reference for the garment and thus enables the position of the garment and the motion of the garment over time to be monitored simply by capturing images of the garment. In this way, a single marker on the garment is not only used to identify the garment but also beneficially allows for the motion of the garment to be monitored. The fiducial marker may be in the form of a 2D image. The fiducial marker of the present invention is beneficial as it is simple, of low cost and does not negatively affect the comfort of the garment for the wearer. The fiducial marker may be an augmented reality (AR) marker with additional information in the form of the code string encoded therein.

The marker may have a limited visual footprint on the garment. This means that the marker may be sufficiently small that it is not easily visible by the naked eye but is still visible in the captured image. In this way, the marker does not affect or has a minimal effect on the appearance of the garment. In some examples, the marker is visible to the naked eye.

The method may further comprise processing the image to determine the location of the fiducial marker.

The method may further comprise displaying a representation of the activity data on a display. The display may be part of the user electronic device or may be communicatively coupled to the user electronic device.

The position of the representation of the activity data on the display may be determined according to the determined location of the fiducial marker.

The position of the representation of the activity data may be determined by applying a predetermined displacement to the coordinate location of the fiducial marker.

The position of the representation of the activity data may correspond to the position of a feature of interest on a wearer of the garment.

The method may further comprise simultaneously displaying a representation of a wearer of the garment with the representation of the activity data on the display. The representation of the activity data may at least partially overlay the displayed representation of the wearer. Beneficially, the display of the activity data is enhanced by positioning the activity data over the representation of the wearer so that the user can understand the relationship between the activity data and a relevant physiological component of the wearer.

Displaying the representation of the wearer of the garment may comprise displaying the obtained image. The obtained image may be a live view image. That is the camera may capture live view image data which may then be displayed on the display of the user electronic device. The user may therefore view a live view image of the wearer.

Displaying the representation of the wearer of the garment may comprise displaying an avatar representation of the wearer. The avatar representation of the wearer may be a 3D representation of the wearer. The avatar may be animated to mimic the motion of the wearer. The avatar may be animated based on motion data obtained from one or more motion sensors of the garment.

The representation of the activity data may represent a physiological or emotional state of the wearer. The physiological state may relate to a muscle or muscle group of the wearer, an organ of the wearer such as the heart or lung(s), or a condition such as the wearer's hydration level. The representation of the activity data my relate to neurological data. The emotional state of the wearer may relate to the stress level of the wearer for example.

The activity data may comprise activity data related to a muscle or muscle group of a wearer of the garment. The position of the representation of the activity data may be determined to correspond to an estimated location of the muscle or muscle group of the wearer as determined from the location of the fiducial marker. The method may comprise simultaneously displaying a representation of the wearer with the representation of the activity data. The representation of the activity data may be displayed such that it overlays the representation of the wearer at the position corresponding to the estimated location of the muscle or muscle group of the wearer.

The muscle or muscle groups may comprise one or more of the triceps, deltoids, pectorals, abdominals, quadriceps, hamstrings, gluteals, and forearms.

The representation of the activity data may represent a physiological state of the muscle or muscle group such as whether the muscle or muscle group are in contraction or relaxation. The representation of the activity data may convey information relating to the activity level of the muscle or muscle group such that the representation may have a darker or lighter colour depending on the intensity of the activity performed by the user.

The activity data may comprise cardiac activity data. The position of the representation of the activity data may be determined to correspond to an estimated location of the heart of a wearer of the garment as determined from the location of the fiducial marker. The method may comprise simultaneously displaying a representation of the wearer with the representation of the activity data. The representation of the activity data may be displayed such that it overlays the representation of the wearer at the position corresponding to the estimated location of the heart of the wearer.

The representation of the activity data may represent a physiological state of the heart such as the heart rate.

The representation of the activity data may be in the form of an augmented reality object.

The representation of the activity data may be in the form of a 2D or 3D object of a feature of interest of the wearer such as a muscle, muscle group or organ. The object may be in the form of a 2D or 3D model of a heart. The model of the heart may be animated to beat at a rate corresponding to the heart rate of the wearer as determined from the activity data.

The obtained image may be captured by a camera that is communicatively coupled to the user electronic device. The camera may capture a live view image. That is, a real-time view otherwise known as a live video feed. Obtaining the image may therefore comprise capturing the image by a camera that is communicatively coupled to the user electronic device. The camera may be part of the user electronic device. The user electronic device may perform the step of processing the image to generate the data string from the visual symbol. Alternatively, the user electronic device may transmit the image to another electronic device to perform the step of processing.

According to a second aspect of the invention, there is provided a method performed by a user electronic device. The method comprises obtaining an image of a garment. The garment comprises a marker located on an outside surface of the garment. The marker comprises a code string identifying the garment encoded into a visual symbol. The method comprises processing the image to generate a data string representing the visual symbol. The method comprises using the data string to access activity data associated with a sensor of the garment identified by the code string.

Using the data string to access activity data associated with a sensor of the garment identified by the code string may comprise the user electronic device transmitting the data string to a server so that the server is able to establish the identity of the garment from the data string. The user electronic device may receive, from the server, the activity data.

The method may further comprise the user electronic device obtaining a user credential from a user. The activity data may only be accessed if the user is authorised, based on the obtained user credential, as having permission to access the activity data.

The method may further comprise the user electronic device transmitting the user credential to a server so that the server is able to determine if the user is authorised as having permission to access the activity data based on the obtained user credential. Using the data string to access the activity data may further comprise the user electronic device receiving, from the server, the activity data if the user is authorised the server as having permission to access the activity data.

According to a third aspect of the invention, there is provided a method performed by a server. The method comprises receiving, from a user electronic device, a data string representing a visual symbol located on an outside surface of a garment, wherein the visual symbol comprises a code string that is encoded into the visual symbol. The method comprises establishing, by the server, the identity of the garment using the received data string. The method comprises providing, to the user electronic device, activity data associated with a sensor of the identified garment.

Establishing, based on the data string, the identity of the garment may comprises decoding the data string so as to obtain the code string and may further comprises identifying the garment based on the code string. The data string may be a digitised representation of the visual symbol or may be an encrypted version of the code string. The method may run a decoding algorithm to generate the code string from the data string.

The method may further comprise receiving a user credential from a user electronic device. The activity data may only be accessed if the user is authorised, based on the obtained user credential, as having permission to access the activity data. In this way, access to the activity data is controlled such that only a user with the requisite user credentials is able to access the activity data.

The method may further comprise determining, based on the obtained user credential, whether the user is authorised to access the activity data. The method may further comprise providing the activity data to the user only if the user is authorised.

According to a fourth aspect of the invention, there is provided a garment. The garment comprises a sensor arranged to monitor the activity of the wearer of the garment. The garment comprises a communication unit arranged to receive activity data for the wearer from the sensor and transmit the activity data to an external device. The garment comprises a marker located on an outside surface of the garment. The marker comprises a code string identifying the garment encoded into a visual symbol and arranged such that, when imaged by an image capturing device, the at least one marker is useable to access activity data associated with the sensor of the garment.

The garment may be suitable for the method of the first, second or third aspect of the invention.

The marker may be a 2D image. The marker may be a fiducial marker optionally in the form of a 2D image. The marker may be an Augmented Reality (AR) marker with additional information in the form of the code string encoded therein.

The marker may comprise a plurality of markers. The plurality of markers may be located at different locations on the garment. The plurality of markers may be arranged in a geometric pattern. The plurality of markers may be arranged together on the garment to form a decorative item.

The plurality of markers may be located at different locations on the garment.

The marker may be integrated into the garment.

The marker may be printed onto the garment. Any known garment printing technique may be used such as screen printing or inkjet printing. The marker may be incorporated onto the garment using a direct to garment printing technique.

The marker may be incorporated into the stitching of the garment, and/or a seam of the garment, and/or a hem of the garment, and/or a neckline of the garment, and/or a collar of the garment, and/or a sleeve of the garment, and/or a cuff of the garment, and/or a pocket of the garment, and/or a body of the garment, and/or a fastener of the garment. The fastener may be a zipper, button, clasp, toggle, stud, snap fastener, popper, eyelet, buckle, tie or ribbon.

The sensor may comprise a plurality of sensors.

The sensor may be arranged to sense one or more signals external to the wearer. The sensor may be any or a combination of a temperature sensor, a camera, a location tracking module such as a GPS module, and a chemical sensor.

The sensor may be a biosensor arranged to measure one or more biosignals of a user wearing the wearable article. Here, biosignal" may refer to any signal in a living being that can be measured and monitored. The term "biosignal" is not limited to electrical signals and can refer to other forms of non-electrical biosignals. The biosensor may be used for measuring one or a combination of bioelectrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer's sweat. The biomechanical measurements include blood pressure. The bioacoustics measurements include phonocardiograms (PCG). The biooptical measurements include orthopantomogram (OPG). The biothermal measurements include skin temperature and core body temperature measurements. The biosensor may comprise a radar unit. The garment may sense a combination of external signals and biosignals of the wearer.

In some examples, the marker has a limited visual footprint on the garment. This means that the marker is sufficiently small that it is not easily visible by the naked eye but is still visible in the image captured by the image capturing device. In this way, the marker does not affect or has a minimal effect on the appearance of the garment. In some examples, the marker is visible to the naked eye.

The marker may be incorporated into or form part of visual element on the garment which may be a decorative item in the garment. The decorative item may be a logo, design, image, motif or pattern on the garment. In this way, the marker may contribute to or enhance the appearance of the garment.

The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, personal protection equipment, swimwear, wetsuit or drysuit. The garment may be constructed from a woven or a non-woven material.

The garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the garment. Polyester, polycotton, nylon and viscose are synthetic fibres that may be used in the garment. The garment may be a tight-fitting garment. Beneficially, a tight-fitting garment helps ensure that any sensors of the garment are held in contact with or in the proximity of a skin surface of the wearer. The garment may be a compression garment. The garment may be an athletic garment such as an elastomeric athletic garment.

The garment may be a shirt. The marker may be located on the collar, yoke, sleeve, gauntlet, cuff, body, pocket, plackett, or fastener of the shirt. The shirt may comprise a plurality of markers. The plurality of markers may be located at a plurality of different positions on the shirt. The plurality of different positions on the shirt may comprise one or more of the collar, yoke, sleeve, gauntlet, cuff, body, pocket, plackett, or fastener of the shirt The garment may be a T-shirt. The marker may be located on the neckline, sleeve, cuff, body or hem of the T-shirt. The T-shirt may comprise a plurality of markers. The plurality of markers may be located at a plurality of different positions on the T-shirt. The plurality of different positions on the shirt may comprise one or more of the neckline, sleeve, cuff, body or hem of the T-shirt.

The communication unit may be a mobile/cellular communicator operable to communicate the data wirelessly via one or more base stations. The communication unit may provide wireless communication capabilities for the garment and enables the garment to communicate via one or more wireless communication protocols such as used for communication over: a wireless wide area network (WWAN), a wireless metroarea network (WMAN), a wireless local area network (WLAN), a wireless personal area network (WPAN), Bluetooth Low Energy, Bluetooth Mesh, Bluetooth 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communication units may be provided for communicating over a combination of different communication protocols.

According to a fifth aspect of the invention, there is provided a system. The system comprises the garment of the fourth aspect of the invention. The system comprises one or more electronic devices operable to: obtain an image of the garment; process the image to generate a data string representing the visual symbol; and use the data string to access activity data associated with a sensor of the garment identified by the code string.

According to a sixth aspect of the invention, there is provided a computer program comprising instructions which, when the program is executed by a computer, cause the computer to carry out the method of the first, second, or third aspect of the invention.

According to a seventh aspect of the invention, there is provided a computer readable storage medium comprising instructions which, when executed by a computer, cause the computer to carry out the method of the first, second, or third aspect of the invention.

According to an eighth aspect of the invention, there is provided a user electronic device operable to perform the method of the first or second aspect of the invention.

According to a ninth aspect of the invention, there is provided a server operable to perform the method of the third aspect of the invention.

According to a tenth aspect of the invention, there is provided a method of manufacturing a garment according to the fourth aspect of the invention. The method comprises generating a code string using a random number generator; encoding the code string into a visual symbol; and incorporating the visual symbol onto the garment.

BRIEF DESCRIPTION OF THE DRAWINGS

Examples of the present disclosure will now be described with reference to the accompanying drawings, in which.

DETAILED DESCRIPTION

Figure 1:
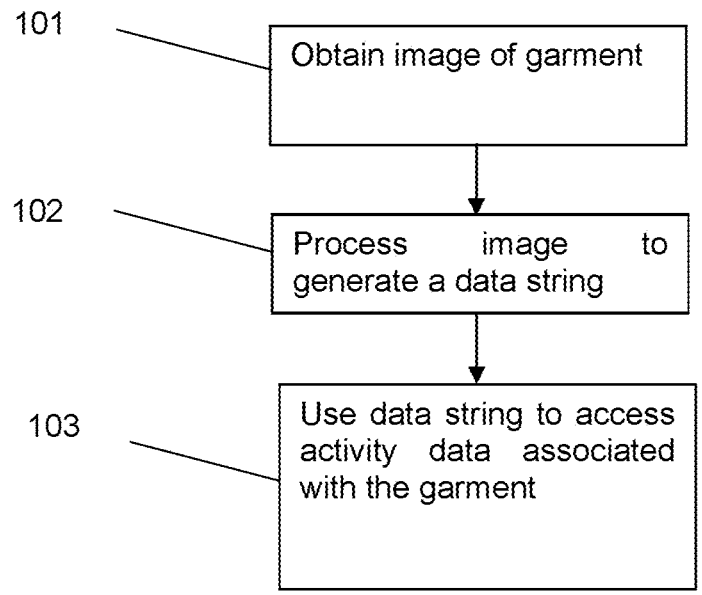
FIG. 1 shows a flow diagram for an example method according to aspects of the present invention.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

According to aspects of the present invention, a garment is provided having a marker located on an outside surface of the garment. The marker comprises a code string identifying the garment encoded into a visual symbol. In more detail, a code is generated for the garment using a random number generator. The code may in a code format with sufficient address space to enable a sufficient number of different codes to be generated. For example, the code format may be in the form of a 14-character hexadecimal number. Once the code is generated by the random number generator, a processor running an algorithm converts the code into a visual symbol which is printed or otherwise manufactured onto the garment. Encoding the code into a visual symbol is beneficial because the original code cannot be parsed from the visual symbol without access to the encoding algorithm. Moreover, the visual symbol is easily machine readable by providing image data of the visual symbol captured using a camera. As an added benefit the visual symbol is also useable as a fiducial marker for tracking the motion of the garment.

The garment further comprises a sensor or more typically a plurality of sensors. The activity data obtained by the sensors is transmitted by a communication unit of the garment to a server. The transmission may be performed over a high throughput wireless communication protocol such as 5G.

The garment may be worn by a first person referred to as the "wearer". A second person referred to as the "user" is in possession of a user electronic device such as a mobile phone. The second person may desire to see activity data for the wearer as recorded by the sensors of the garment. For example, the user may be a personal trainer that may desire to view metrics such as the wearer's heartrate, respiration levels and hydration levels. The user may also be a healthcare professional such as a physiotherapist or doctor.

In some examples, the "user" and the "wearer" refer to the same person. For example, the user electronic device may be a television apparatus with an integrated camera. The wearer of the garment may stand in front of the television apparatus and may be captured by the camera of the television apparatus. The television apparatus may then display the activity data so that the wearer may view their activity information.

Referring to FIG. 1, there is shown an example method according to the first aspect of the present invention that allows the user of to obtain access the activity data via their user electronic device.

In step 101 of the method, the user electronic device obtains an image of the garment. In particular, the second user uses the camera of their user electronic device to capture real time live view images of the wearer as they perform activities while wearing the garment.

In step 102 of the method, the user electronic device processes the image to generate a data string. The user electronic device performs an image processing operation to convert the visual symbol into the data string. The user electronic device may generate the data string by simply digitising the image of the visual symbol. The digitised version of the visual symbol may then be transmitted to a server which decodes the symbol. Alternatively, the user electronic device may translate the visual symbol into an encrypted version of the code string. The encrypted version of the code string may be transmitted by a server for decoding. The user electronic device may decode the data string but it is generally beneficial to keep the decoding algorithm private.

In step 103 of the method, the data string is used by the user electronic device to access activity data associated with the garment. For example, the data string may be used to access activity data for the garment in real time. The activity data may relate to one or more biosignals of the user such as the heart rate, respiration rate and hydration level of the user. In this way, the user is able to obtain biosignal data for the wearer in real time so as to enable the user to observe and assess the performance of the wearer. This is particularly useful when the user is a personal trainer or healthcare professional.

Figure 2:
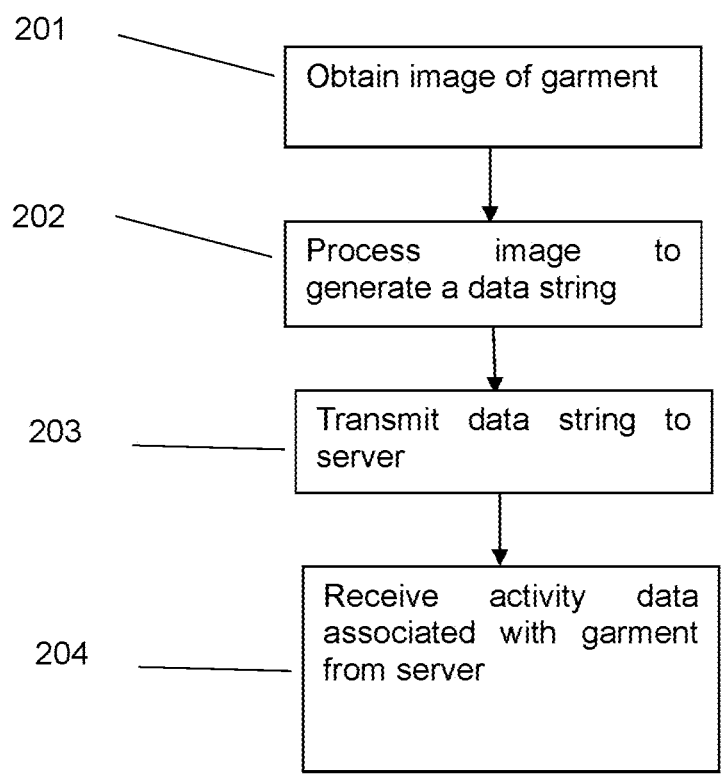
FIG. 2 shows a flow diagram for an example method according to aspects of the present invention.

Referring to FIG. 2, there is shown a more detailed overview of the example method of FIG. 1. In FIG. 2, steps 201 and 202 are the same as steps 101 and 102 in FIG. 1. Step 103 of FIG. 1 is split into two separate steps performed by the user electronic device which are referred to as steps 203 and 204. In step 203, the user electronic device transmits the data string to a server. The server then identifies the garment from the data string and transmits activity data associated with a sensor of the identified garment to the user electronic device. In more detail, the server may decode the data string and compare the decoded data string to the original code string (which may be stored securely on the server) to determine whether the decoded data string matches the code string. The server may store code strings for a number of garments and therefore the decoded data string may be compared against a plurality of code strings stored in the database. If the decoded data string matches a code string in the database, the server may identify the garment associated with the code string and obtain activity data for the identified garment. The activity data may be stored on the server or on another server that is communicatively coupled to the server. In step 204, the user electronic device receives the activity data from the server.

Figure 3:
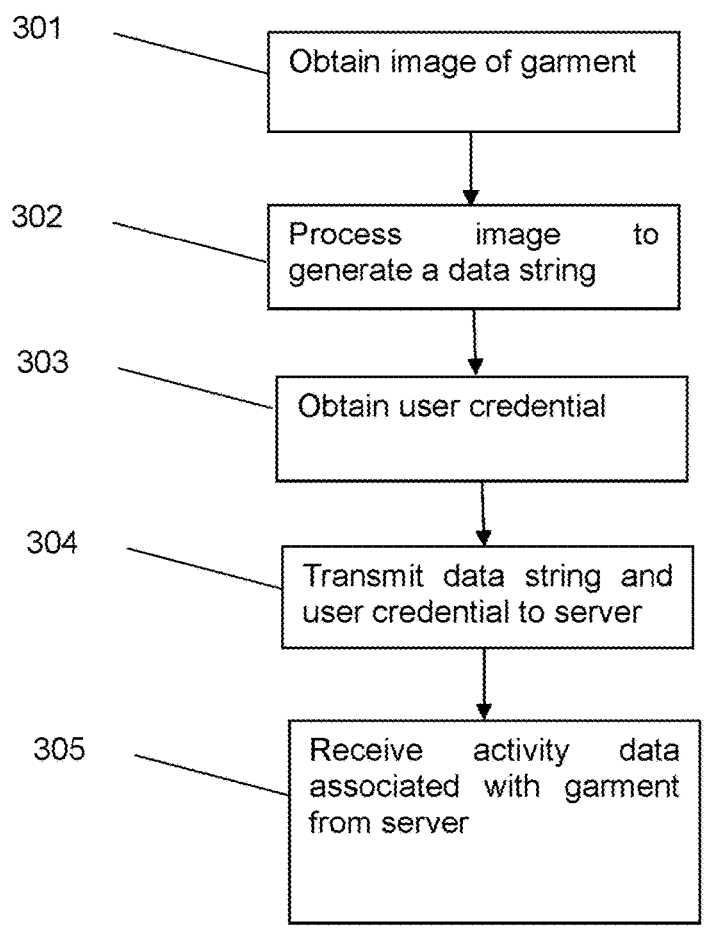
FIG. 3 shows a flow diagram for an example method according to aspects of the present invention.

Referring to FIG. 3, there is shown a more detailed overview of the example method of FIG. 1. In FIG. 3, steps 301 and 302 are the same as steps 101 and 102 of FIG. 1 and steps 201 and 202 of FIG. 2. Step 103 of FIG. 1 is split into three separate steps performed by the user electronic device which are referred to as steps 303, 304 and 305. In step 303, the user electronic device obtains a user credential for the user. The user credential may be in the form of a password or passcode or biometric data. Any form of biometric data may be used such as fingerprint data, ECG data, or iris data. In step 304, the user electronic device transmits the data string and the user credential to the server. The server then identifies the garment from the data string and authenticates the user based on the user credential. In more detail, the server may store the code string associated with the identified garment and the user credential indicating whether the user is authorised to access the activity data. This information may be stored in a database along with code strings for other garments and user credentials for other users. In response to receiving the data string and the user credential, the server decodes the data string and compares the decoded data string to the code string or strings in the database.

If the decoded data string matches a code string in the database, the server identifies the garment associated with the code string. The server then determines based on the received user credential whether the user is authenticated as having permission to access the activity data. Different users may have access to different parts of the activity data for a garment. That is, different users may have different permission levels in relation to the activity data. For example, a personal trainer may have access to a limited amount of activity data for the garment. The personal trainer may have access to heart rate, respiration rate, and hydration level data. The personal trainer may not have access to other activity data which may relate to more personal information. In contrast, a healthcare professional may have access to all of the data for the garment. The access level may be indicated by the user credential. In step 305 the user electronic device receives the activity data from the server.

It will be appreciated that the step of obtaining user credentials is not required in all embodiments of the present invention. For example, if only trusted user electronic devices are able to communicate with the server then a separate step of authorising the user will not always be required.

Figure 4A:
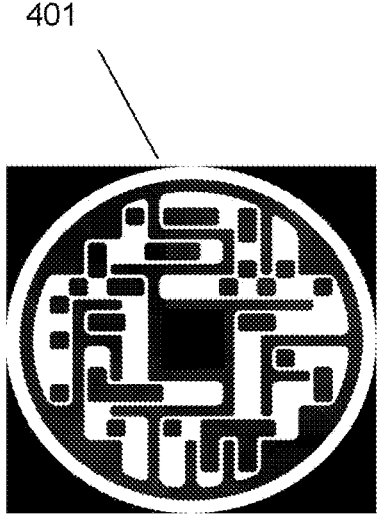
FIGS. 4A and 4B show example markers in accordance with aspects of the present invention.

Referring to FIG. 4A, there is shown an example marker 401 in accordance with the present invention. The marker 401 in this example is based on the Vcode® provided by VST Enterprises™ and comprises a visual symbol in the form of black marks upon white pathways. The black marks represent the characters in the code string. The visual symbol may additionally encode redundant information for error detection, correction, and uniqueness over different rotations of the marker.

Figure 4B:
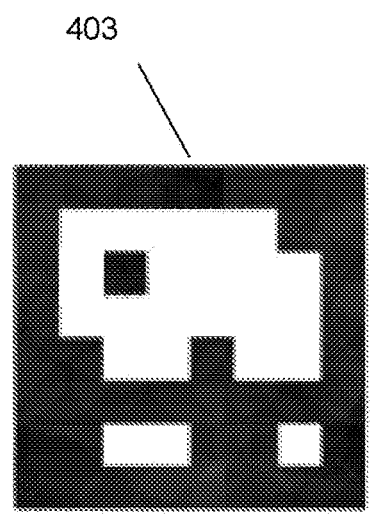

Referring to FIG. 4B, there is shown another example marker 403 in accordance with the present invention. The marker 403 in this example is derived from the AR marker system known as ARTag. The marker 403 comprises a visual symbol in the form of a 6×6 grid of black or white cells which represent 36 binary '0' or '1' symbols. The 36-bit sequence encodes the code string and may additionally encode redundant information for error detection, correction and uniqueness over the different rotations of the marker.

In both examples, the code string/data string may be retrieved from the marker 401, 403 by processing an image containing the visual symbol. It will be appreciated that known image processing operations such as contour extraction and edge detection will be used to read the symbol from the image.

It will be appreciated that the marker 401, 403 in accordance with the present invention is not limited to the examples of markers shown in FIGS. 4A and 4B. Instead, other forms of markers 401, 403 that encode a code string identifying the garment into a visual symbol may be used. In most preferred examples, the markers 401, 403 are additionally used as fiducial markers 401, 403. This means that the markers 401, 403 act as a point of reference for the garment and thus enable the position of the garment and the motion of the garment over time to be monitored simply by capturing images of the garment. Generally, the marker 401, 403 is preferred to be a bitonal marker as this means that there is no need to identify different shades of grey within the marker 401, 403 during the image processing operation to identify and decode the marker 401, 403. This beneficially helps reduce the sensitive to lighting conditions and camera settings. Of course, in some examples the marker 401, 403 may not be bitonal and may comprise different grey levels or indeed different colours.

Figure 5:
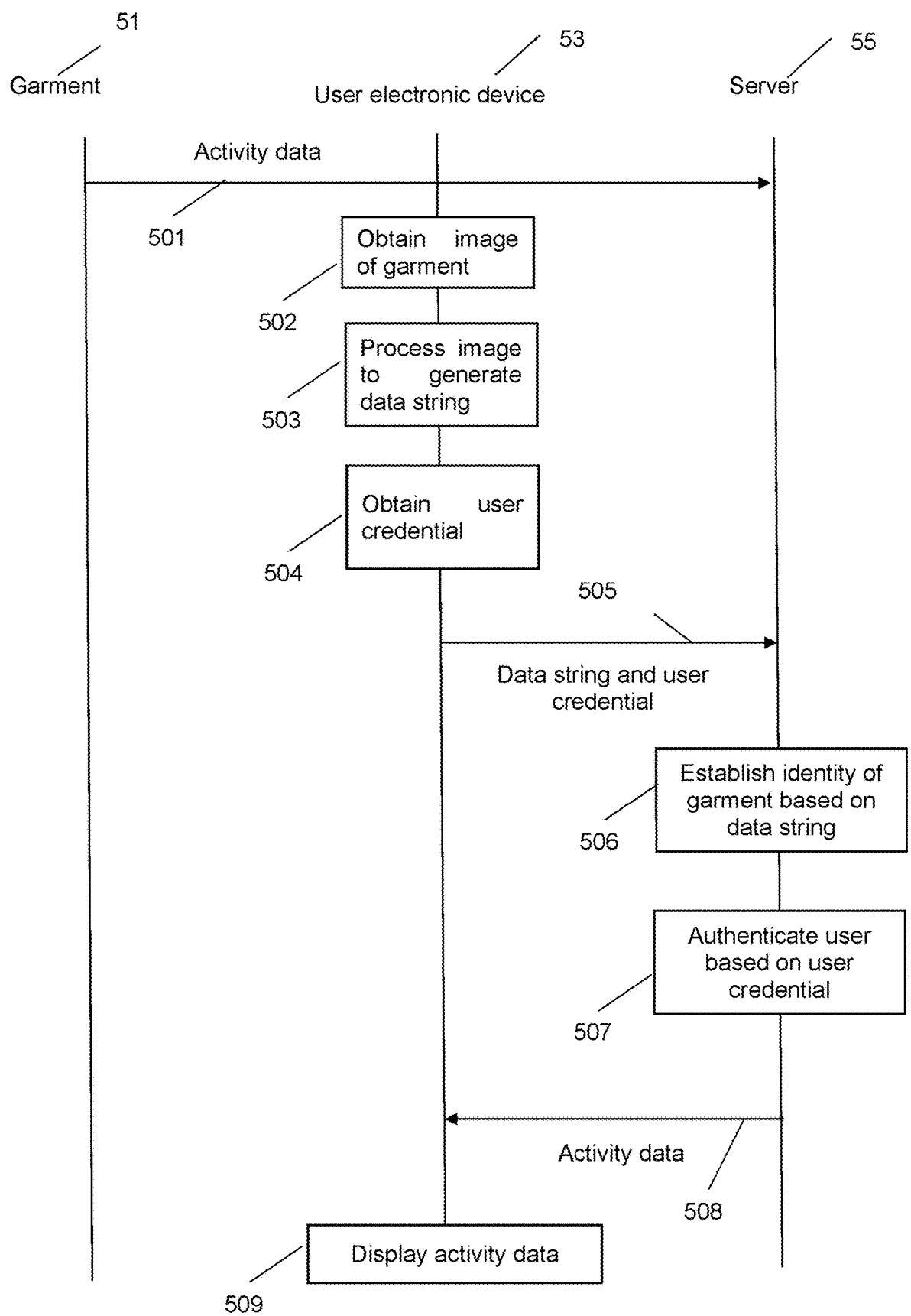
FIG. 5 shows a flow diagram for an example method according to aspects of the present invention.

Referring to FIG. 5, there is shown a more detailed overview of an example method according to aspects of the invention. The method is performed by a garment 51, user electronic device 53, and server 55.

The garment 51 comprises at least one sensor arranged to monitor the activity of the wearer of the garment 51. The garment 51 further comprises a communication unit arranged to receive activity data for the wearer from the at least one sensor and transmit the activity data to the server 55. In step 501 the garment 51 transmits the activity data to the server 55.

In step 502, the user electronic device 53 obtains an image of the garment. In step 503, the user electronic device 53 processes the image to generate a data string. In other examples, the user electronic device 53 does not process the image and instead transmits the image to another electronic device. The other electronic device may process the image to generate the data string. The other electronic device may be the server 55.

In step 504, the user electronic device 53 obtains a user credential for the user. In step 505, the user electronic device 53 transmits the data string and user credential to the server 55. If the user electronic device 53 does not process the image to obtain the data string then only the user credential will be transmitted in step 505.

In step 506, the server 55 establishes the identity of the garment 51 based on the received data string. In step 507, the server 55 authenticates the user based on the received user credential. If the user credential indicates that the user is authenticated to access activity data for the identified garment then the server 55 transmits the relevant activity data to the user electronic device in step 508. The activity data transmitted to the user electronic device 51 may not be the same as the activity data received by the server 55 from the garment 51 in step 501. This is because the server 55 may perform additional processing operations on the activity data. In step 509, the user electronic device 53 displays the activity data, or a representation of the activity data, to the user.

Figure 6:
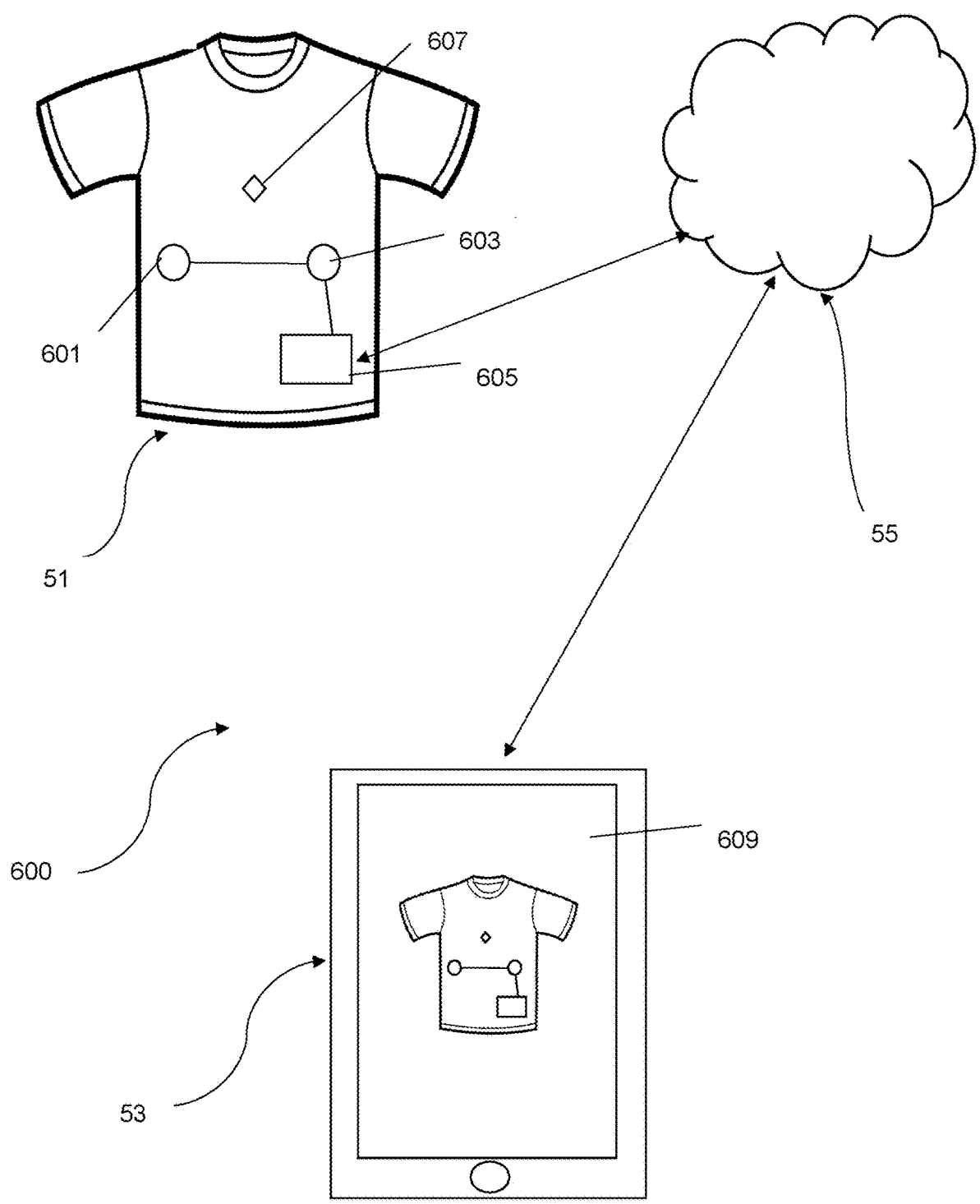
FIG. 6 shows an example system according to aspects of the present invention.

Referring to FIG. 6, there is shown an example garment 51, user electronic device 53, and server 55 in accordance with aspects of the present invention. The garment 51, user electronic device 53, and server 55 form an example system 600 in accordance with aspects of the invention.

The garment 51 in the example of FIG. 6 is in the form of a T-shirt. The garment 51 comprises two sensors 601, 603 arranged to monitor the activity of the wearer of the garment 51. In this example, one of the sensors 601 acts as a monitoring unit and the other sensor 603 acts as a reference unit. The sensors 601, 603 are communicatively coupled to a communication unit 605 arranged to communicate activity data to the server 55. The garment 51 comprises a marker 607 located on the outside surface of the garment 51 and in particular on the main body of the T-shirt. The marker 607 comprises a code string identifying the garment encoded into a visual symbol as shown in FIGS. 4A and 4B. The marker 607 is arranged such that, when imaged by an image capturing device such as the camera of the user electronic device 53, the marker 607 is useable to access activity data associated with the garment 51.

The user electronic device 53 in the example of FIG. 6 is in the form of a mobile phone with an integrated camera. The user electronic device 53 comprises a communication unit, a storage, a controller, a display 609, a camera and a user input unit. The controller provides overall control to the user electronic device. The communication unit transmits and receives various pieces of information required for communication with a server under the control of the controller. The communication unit transmits the data string to the server and receives activity data from the server. The user input unit receives inputs from the user such as a user credential. The camera captured the image of the garment. The storage stores information for the user terminal. The display 609 is arranged to show a live view image of the scene captured by the camera. The display 609 may be a presence-sensitive display and therefore may comprise the user input unit. The presence-sensitive display may include a display component and a presence-sensitive input component. The presence sensitive display may be a touch-screen display arranged to provide the user interface.

The user electronic device 53 may also include a biometric sensor. The biometric sensor may be used to identify a user or users of device based on unique physiological features. The biometric sensor may be: a fingerprint sensor used to capture an image of a users fingerprint; an iris scanner or a retina scanner configured to capture an image of a users iris or retina; an ECG module used to measure the user's ECG; or the camera of the user electronic arranged to capture the face of the user. The biometric sensor may be an internal module of the user electronic device. The biometric module may be an external (stand-alone) device which may be coupled to the user electronic device by a wired or wireless link.

User electronic devices in accordance with the present invention are not limited to mobile phones and may take the form of any electronic device which may be used by a user to perform the methods according to aspects of the present invention. The user electronic device may be a mobile electronic device such as a smartphone, tablet personal computer (PC), mobile phone, smart phone, video telephone, laptop PC, netbook computer, personal digital assistant (PDA), mobile medical device, camera or wearable device. The wearable device may include a head-mounted device such as an Augmented Reality, Virtual Reality or Mixed Reality head-mounted device. The user electronic device may be desktop PC, workstations, television apparatus or a projector, e.g. arranged to project a display onto a surface.

The server 55 may be a single device or may comprise a plurality of distributed devices communicatively coupled to one another, e.g. as a cloud-based server such as cloud server network. The server comprises a communication unit, a storage, and a controller. The controller provides overall control to the server. The communication unit transmits and receives various pieces of information required for communication with a user electronic device and/or garment under the control of the controller. The storage stores information for the server such as code strings identifying garments and user credential information.

Figure 7:
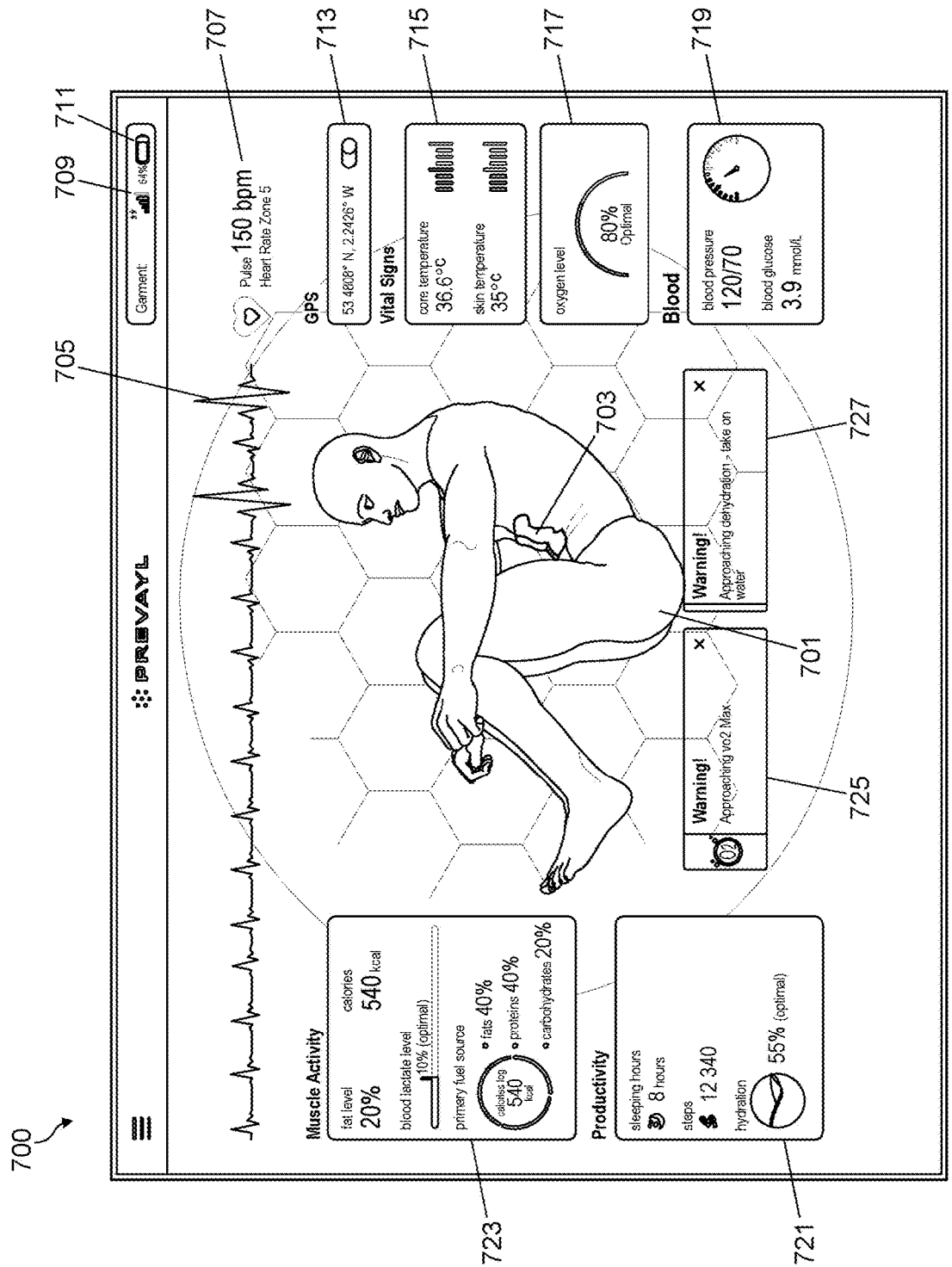
FIG. 7 shows an example user interface according to aspects of the present invention.

Referring to FIG. 7, there is shown an example user interface 700 displayed on the user electronic device 53.

The user interface includes a display of a representation of the wearer of the garment 701. In this example, the representation of the wearer of the garment 701 is in the form of a 3D avatar. The 3D avatar will move as the wearer moves as a result of the motion tracking performed using the fiducial markers provided on the garment 51. A more refined motion estimate may be provided by incorporating additional active motion sensors such as accelerometers and gyroscopes into the garment. In other examples, the displayed representation of the wearer of the garment 701 is in the form of a live view image as captured by the camera of the user electronic device 53. In this example, the additional active motion sensors are not required for the garment 51 but may still be provided.

The user interface 700 also includes representation of the activity data 703 received from the server 55. The representation of the activity data 703 in this example is the form of an object 703 that overlays the abdominal muscles of the wearer. The representation of the activity data 703 changes colour depending on whether the activity data indicates that the abdominal muscles are in contraction or relaxation. In FIG. 7, the abdominal muscles are in contraction and as such the object 703 has a dark colour. When the abdominal muscles are in relaxation the colour of the object 703 lightens. Of course, other visual representations of the activity data relating to the abdominal muscles may be provided.

The object 703 is displayed at a position determined according to the location of the marker on the garment 51. In particular, the marker is a fiducial marker that acts as a reference position for the garment 51 in relation to the wearer of the garment 51. The position of the object to be displayed is determined using the position of the marker (x1, y1) in the image and a predetermined displacement (x2, y2) from the marker to a feature of interest on the wearer such as the abdominal muscles. In particular, the position of the object 703 to be displayed can be determined as (x1, y1)+(x2, y2).

The user interface 700 of FIG. 7 displays additional activity data for the wearer and other data for the garment 51 at positions which are not determined based on the location of the marker on the garment 51. The user interface 700 includes an ECG trace 705 and heartrate data 707; the signal strength 709 for the communication unit of the garment 51; the battery level 711 for a battery of the garment 51; GPS coordinate data 713; core body temperature and skin surface temperature 715; the oxygen level 717, blood pressure and blood glucose levels 719, sleep tracking, step tracking and hydration level 721, and fat level, calories burned, blood lactate level as well as an indication of the type of calories burned 723. The user interface 700 also displays warnings 725, 727 indicating the wearer's VO2 and hydration levels are concerning. Of course, the user interface 700 in FIG. 7 is just one example interface and other forms of bio data may be displayed to the user in a different way.

Figure 8:
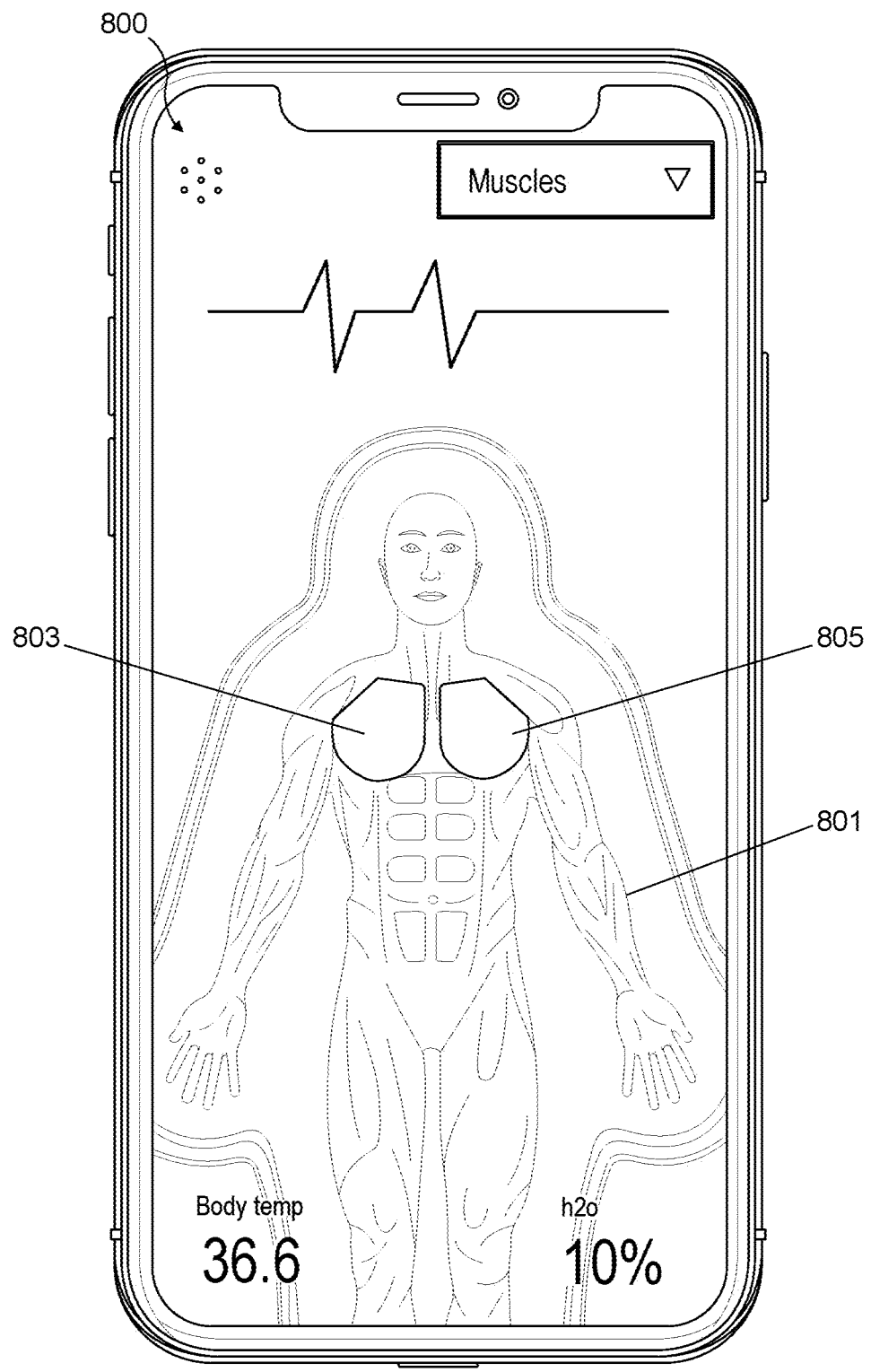
FIG. 8 shows an example user interface according to aspects of the present invention.

Referring to FIG. 8, there is shown another example user interface 800 displayed on the user electronic device 53. The user interface 800 displays a representation of the wearer 801 which may be a 3D avatar or a live view image of the wearer. In addition, the user interface 800 overlays the representation of the wearer 801 with two objects 803, 805. The two objects 803, 805 are displayed at positions that correspond to the location of the pectoral muscle area of the wearer. The position of the objects 803, 805 are determined according to the location of the marker on the garment as described above in relation to FIG. 7. The objects 803, 805 are representations of the activity data of the wearer relating to the pectoral muscle area. The objects 803, 805 change colour based on the received activity data for example to indicate whether the muscles are in contraction or relaxation.

Figure 9:
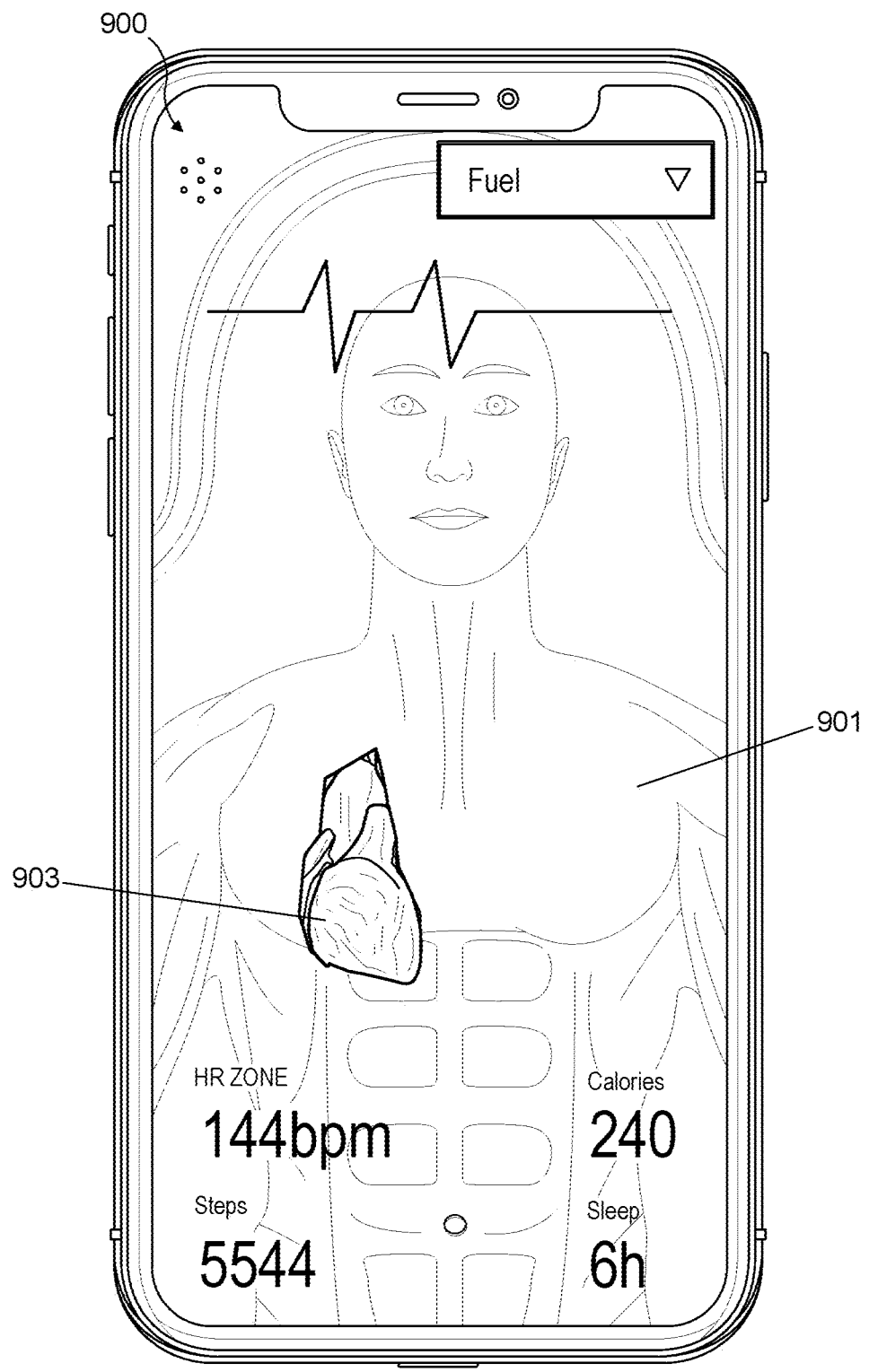
FIG. 9 shows an example user interface according to aspects of the present invention.

Referring to FIG. 9, there is shown another example user interface 900 displayed on the user electronic device 53. The user interface 900 displays a representation of the wearer 901 which may be a 3D avatar or a live view image of the wearer. In addition, the user interface 900 overlays the representation of the wearer 901 with an object 903. The object 903 is displayed at a position that corresponds to the location of the heart (the representation of the wearer 901 is displayed as a mirror image in FIG. 9). The position of the object 903 is determined according to the location of the marker on the garment as described above in relation to FIG. 7. The object 903 is a representation of the cardiac activity data of the wearer. The object 903 is in particular an animated 3D model of a heart that beats at a rate corresponding to the heart rate of the wearer as determined from the activity data.

In addition, the user interface may display information relating to past or predicted future movements undertaken by the wearer. The garment may incorporate one or more motion sensors such as accelerometers or gyroscopes which may be used to derive position and velocity data for the wearer. This information may be displayed such that the user can view how the wearer has moved over time. Moreover, based on past motion information a future motion of the user may be estimated and displayed. The motion information may be displayed as a series of points on the display such as in the form of a point cloud.

Figure 10:
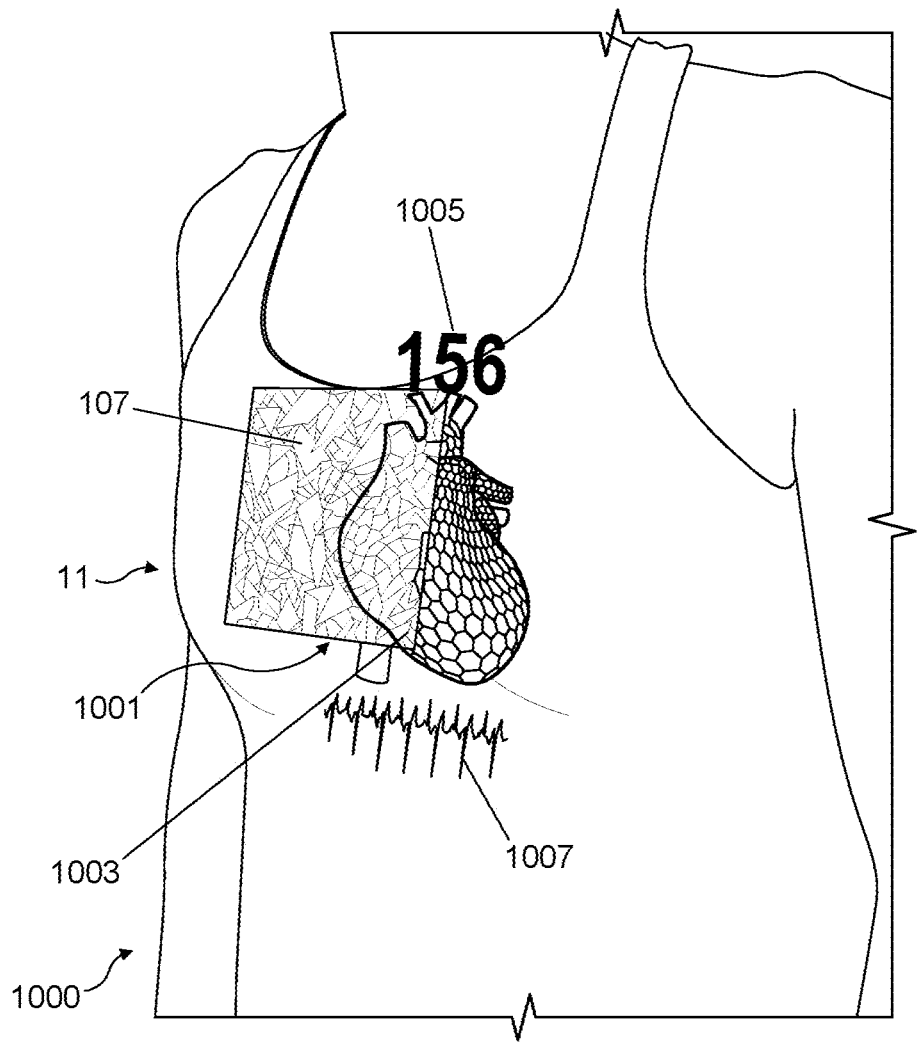
FIG. 10 shows an example user interface according to aspects of the present invention.

Referring to FIG. 10, there is shown an example user interface according to aspects of the present invention. The user interface displays a live view image 1000 that is captured by a camera communicatively coupled to the electronic device. The live view image 1000 is a live video feed of the wearer wearing the garment 11. The garment 11 has a fiducial marker 107 located on an outside surface of the garment. The live view image 1000 is processed to determine the location of the fiducial marker 107. The display of the live view image 1000 is augmented with the display of an augmented reality object 1001. The position of the augmented reality object 1001 on the display is determined based on the determined location of the fiducial marker 107. That is, the augmented reality object 1001 is always displayed at a predetermined displacement from the fiducial marker 107. The effect of this is that the augmented reality object 1001 always appears on the display to overlay the cardiac region of the wearer of the garment 11. The augmented reality object 1001 provides a representation of the cardiac activity data which is recorded by one or more sensors (not visible) of the garment. The augmented reality object 1001 comprises a 3D model of the heart 1003 that is animated to beat at a rate corresponding to the heart rate of the wearer as recorded by the sensor(s) of the garment 11, The 3D model of the heart 1003 changes colour based on the heart rate of the wearer. The 3D model of the heart 1003 is green when the heart rate is at a low value (e.g. less than 100 beats per minute), yellow when the heart rate is at a medium value (e.g. between 100 and 145 beats per minute) and red when the heart rate is at a high value (e.g. greater than 145 beats per minute). Of course, other colours may be used. The 3D model of the heart may additionally or separately change size, shape or texture depending on the heart rate. The augmented reality object 1001 comprises a numerical display of the heart rate 1005. The augmented reality object 1001 comprises a display of ECG data 1007 for the wearer. The display of the heart rate 1005 and the ECG data 1007 may also change colour, size, shape or texture depending on the heart rate. Conveniently, the present invention conveys cardiac information to the observer in a way that is easy and intuitive to understand as the augmented reality object 1001 is always positioned to overlay the cardiac region of the wearer.

In an example use case, a garment according to the present disclosure is worn by a patient visiting a medical professional such as a doctor. The doctor uses an electronic device to scan the marker located on the outside surface of the garment. As a result, the electronic device is able to obtain activity data associated with a sensor of the garment identified by the code string. The activity data may be real-time data sensed by the sensor or may be historic data stored in a memory of the garment or on a separate data store. In this way, the medical professional is provided with a simple and convenient method for accessing physiological data for the patient to aid in the medical professional providing medical care.

In an example use case, a garment according to the present disclosure is worn by a subject who has undergone a medical emergency and may be unresponsive. A medical professional such as a first aid responder or medic is able to scan the marker located on the outside surface of the garment so as to obtain activity data to aid in providing medical care to the subject. Beneficially, the marker located on the outside surface of the garment may be clearly visible to the medical professional so as to visually indicate that they are able to download data. In a particular example, the medical professional may be able to download motion data recorded by an inertial measurement unit of the garment so as to determine what g-forces were experienced by the subject. This is beneficial after a road accident or a collision between players in a sporting event for example.

In an example use case, a sports coach may desire to monitor several players on a team. The coach is able to use an electronic device to scan the marker located on the outside surface of the garment of the player to obtain activity data for the player. This enables the coach to quickly and easily ascertain information about the player related to their performance.

In summary, there is provided a method, garment and system. An image of a garment is obtained. The garment comprises a marker located on an outside surface of the garment. The marker comprises a code string identifying the garment encoded into a visual symbol. The image is processed to generate a data string representing the visual symbol. The data string is used to access activity data associated with a sensor of the garment identified by the code string. The system comprises the garment and one or more electronic devices operable to perform the method.

While the particular examples mentioned above refer to wearable articles in the form of garments, it will be appreciated that the present disclosure is not limited to such examples and other forms of wearable article are within the scope of the present disclosure. The wearable article may be, for example, any form of electronic device which may be worn by a user such as a smart watch, necklace, bracelet, or glasses. The wearable article may be a textile article.

While the particular examples mentioned above refer to visual symbols located on an outside surface of a garment or other form of wearable article, it will be appreciated that the present disclosure is not limited to such examples. Other forms of visual symbol which are readable from the outside of the garment but not necessarily provided on the outside surface of the garment are within the scope of the present disclosure.

In some examples according to the present disclosure, electronics components of the garment such as the communication unit and sensor are removable from the garment. The electronics components may be removably contained within a pocket of the garment.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method comprising:
pairing a user electronic device with an electronics module so as to enable communication between the user electronic device and the electronics module, the electronics module being removably attached to a garment, and the garment further comprising a sensor associated with the garment and arranged to obtain physiological data from a wearer of the garment;
capturing, using the user electronic device, an image of the garment and a visual symbol located on an outside surface of the garment, the visual symbol comprises a code string identifying the garment encoded into the visual symbol;
processing, using the user electronic device, the captured image including the visual symbol to generate a data string representing the visual symbol from the captured image;
decoding the data string using the user electronic device, so as to obtain the code string;
establishing the identity of the garment from the obtained code string;
obtaining real time physiological data from the wearer of the identified garment using the sensor associated with the identified garment and the electronics module;
obtaining a user credential from a user, using the user electronic device;
determining, based on the obtained user credential, whether the user is authorised to access the real time physiological data;
accessing, using the user electronic device, the obtained real time physiological data if the user is authorised, based on the obtained user credential, as having permission to access the real time physiological data; and presenting a representation of the obtained real time physiological data to the authorised user using the user electronic device.

2. The method of claim 1, wherein the step of accessing the obtained real time physiological data from the sensor associated with the identified garment comprises: transmitting the code string to a server so that the server is able to establish the identity of the garment from the code string; and receiving, from the server, the real time physiological data associated with the sensor of the identified garment.

3. The method of claim 2, further comprising transmitting the user credential to the server so that the server is able to determine if the user is authorised as having permission to access the real time physiological data based on the obtained user credential, and wherein using the code string to access the real time physiological data further comprises receiving, from the server, the real time physiological data if the user is authorised by the server as having permission to access the real time physiological data.

4. The method of claim 1, wherein the visual symbol is a fiducial marker.

5. The method of claim 4, further comprising processing the image to determine the location of the fiducial marker.

6. The method of claim 5, further comprising displaying a representation of the real time physiological data on a display, and wherein the position of the representation of the real time physiological data on the display is determined according to the determined location of the fiducial marker.

7. The method of claim 6, wherein the position of the representation of the real time physiological data is determined by applying a predetermined displacement to the coordinate location of the fiducial marker.

8. The method of claim 6, further comprising simultaneously displaying a representation of the wearer of the garment with the representation of the real time physiological data on the display.

9. The method of claim 6, wherein the representation of the real time physiological data at least partially overlays the displayed representation of the wearer.

10. The method of claim 6, wherein displaying the representation of the wearer of the garment comprises displaying the obtained image.

11. The method of claim 6, wherein displaying the representation of the wearer of the garment comprises displaying an avatar representation of the wearer.

12. The method of claim 6, wherein the representation of the real time physiological data is in the form of an augmented reality object.

13. The method of claim 1, further comprising:
pairing the user electronic device with a second electronics module so as to enable communication between the user electronic device and the second electronics module;
while the obtained real time physiological data is being accessed and the representation of the obtained real time physiological data is being presented in real time, capturing, using the user electronic device, a second image of a second garment and a second visual symbol located on an outside surface of the second garment, wherein the second visual symbol comprises a second code string identifying the second garment encoded into the second visual symbol, and wherein the second garment comprises the second electronics module removably attached to the second garment and coupled to a second sensor associated with the second garment and arranged to obtain second physiological data from a wearer of the second garment;
processing, using the user electronic device, the captured second image including the second visual symbol to generate a second data string representing the second visual symbol from the captured second image;
decoding the second data string using the user electronic device, so as to obtain the second code string;
establishing the identity of the second garment from the obtained second code string;
obtaining second real time physiological data from the wearer of the identified second garment using the second sensor instead of obtaining the real time physiological data from the wearer of the identified garment using the sensor;
determining, based on the obtained user credential, whether the user is authorised to access the real time second physiological data;
accessing, using the user electronics device, the obtained real time second physiological data if the user is authorised, based on the obtained user credential, as having permission to access the second real time physiological data; and
presenting a representation of the obtained second real time physiological data to the authorised user, in place of the representation of the obtained physiological data, using the user electronic device.

14. The method of claim 1, wherein pairing the user electronic device with the electronics module is based on the obtained code string.

15. The method of claim 1, further comprising listening, using the user electronic device, for the real time physiological data based on the obtained code string.

16. A method performed by a server, the method comprises:
receiving, from a user electronic device, a data string representing a visual symbol located on an outside surface of a garment, wherein the visual symbol comprises a code string identifying the garment that is encoded into the visual symbol;
decoding the data string so as to obtain the code string;
establishing the identity of the garment based on the obtained code string;
receiving real time physiological data obtained by a sensor provided on the garment and transmitted to the server;
associating the sensor with the identified garment;
receiving a user credential, from a user, from the user electronic device;
authenticating the user, based on the received user credential, for access to the real time physiological data; and
providing, to the user electronic device for presentation to the user in real time, the obtained physiological data obtained by the sensor associated with the identified garment, when the user is authenticated for access to the real time physiological data.

17. A system comprising a garment, the garment comprising an associated sensor arranged to monitor the physiological activity of the wearer of the garment; a communication unit arranged to receive real time physiological data for the wearer from the sensor and to transmit the real time physiological data to an external device; and at least one visual symbol located on an outside surface of the garment, the at least one visual symbol comprising a code string identifying the garment encoded into the visual symbol and arranged such that, when captured by an image capturing device, the at least one visual symbol is useable to access real time physiological data associated with the sensor of the garment, the system further comprising one or more electronic devices operable to:
- capture an image of the garment including the visual symbol;
- process the captured image to generate a data string representing the visual symbol;
- decode the data string so as to obtain the code string;
- establish the identity of the garment based on the obtained code string;
- obtain the real time physiological data using the sensor associated with the identified garment;
- obtain a user credential from a user;
- determine, based on the obtained user credential, whether the user is authorised to access the real time physiological data;
- access the obtained physiological data if the user is authorised, based on the obtained user credential, as having permission to access the real time physiological data; and
- present a representation of the obtained real time physiological data to the authorised user.

\* \* \* \* \*